(12) United States Patent
Bendsen et al.

(10) Patent No.: US 7,407,490 B2
(45) Date of Patent: Aug. 5, 2008

(54) DELIVERY DEVICE AND CARTRIDGE THEREFORE

(75) Inventors: Henrik Bendsen, Copenhagen V (DK); Jens Moller-Jensen, Copenhagen K (DK)

(73) Assignee: Novo Nordisk A/S, Bagsvaerd (DK)

( * ) Notice: Subject to any disclaimer, the term of this patent is extended or adjusted under 35 U.S.C. 154(b) by 1061 days.

(21) Appl. No.: 10/301,461

(22) Filed: Nov. 21, 2002

(65) Prior Publication Data

US 2003/0100864 A1    May 29, 2003

Related U.S. Application Data

(60) Provisional application No. 60/337,914, filed on Dec. 6, 2001.

(30) Foreign Application Priority Data

Nov. 29, 2001    (DK)    ............................... 2001 01769

(51) Int. Cl.
*A61M 37/00*    (2006.01)

(52) U.S. Cl. ............................................. 604/131

(58) Field of Classification Search ......... 604/131–133, 604/142, 148, 150, 156, 81, 82, 181, 187
See application file for complete search history.

(56) References Cited

U.S. PATENT DOCUMENTS

| 4,468,221 A |   | 8/1984 | Mayfield ................. 604/152 |
|---|---|---|---|
| 4,718,430 A | * | 1/1988 | Holzer ................. 600/365 |
| 4,753,651 A | * | 6/1988 | Eckenhoff ................. 424/449 |
| 5,480,386 A |   | 1/1996 | Brohy et al. ................. 604/131 |
| 5,527,288 A |   | 6/1996 | Gross et al. ................. 604/140 |
| 5,928,196 A |   | 7/1999 | Johnson et al. ................. 604/153 |
| 5,938,640 A |   | 8/1999 | Maget et al. ................. 604/145 |
| 6,258,063 B1 |   | 7/2001 | Haar et al. ................. 604/141 |

FOREIGN PATENT DOCUMENTS

| DE | 37 39 657 | 5/1988 |
|---|---|---|
| EP | 0 197 179 | 11/1988 |
| WO | 97/21457 | 6/1997 |
| WO | 00/10630 | 3/2000 |

* cited by examiner

*Primary Examiner*—Kevin C. Sirmons
(74) *Attorney, Agent, or Firm*—Marc A. Began

(57) ABSTRACT

The invention relates to a portable pump device and a cartridge therefore. The cartridge comprises a first reservoir for a flowable drug provided in combination with a second reservoir comprising a pump liquid, a pump chamber being associated with the first reservoir and adapted to receive the pump liquid in order to expel drug from the first reservoir. In a first aspect, the reservoirs of the system may be provided as a disposable cartridge unit to be combined with a further unit to form an delivery device, the delivery device as a whole comprising the pump means for pumping the pump liquid from the second reservoir to the pump chamber, control means for controlling the action of the pump means, and an energy reservoir for energizing the pump means as well as the control means, however, one or more of these components may be incorporated in the disposable cartridge.

16 Claims, 3 Drawing Sheets

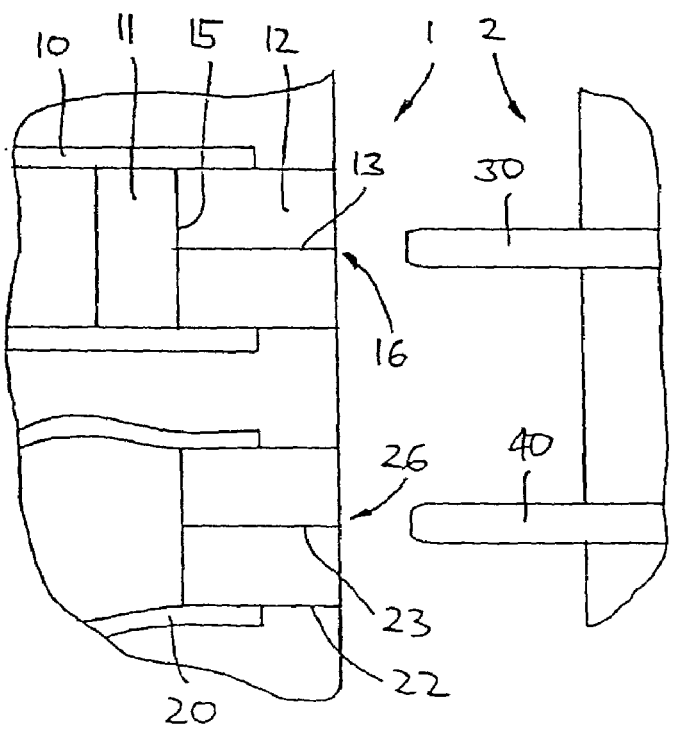
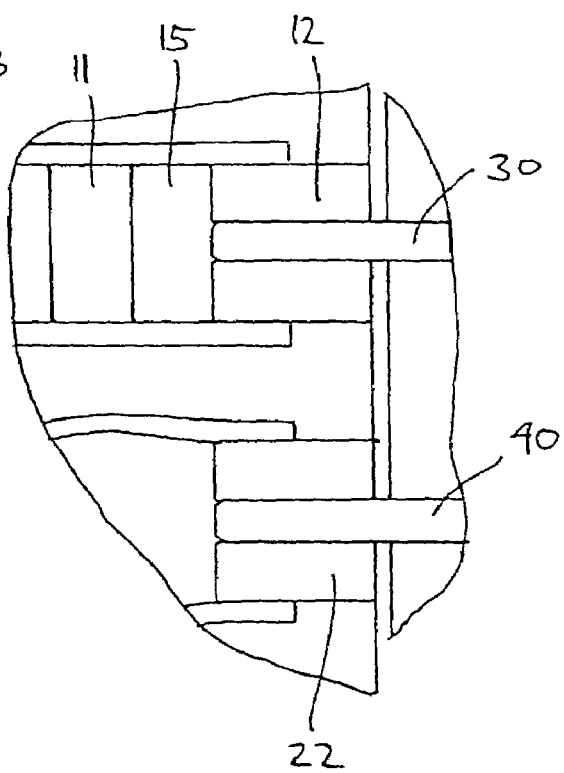

DELIVERY DEVICE AND CARTRIDGE THEREFORE

CROSS-REFERENCE TO RELATED APPLICATIONS

This application claims priority under 35 U.S.C. §119 of Danish application no. PA 2001 01769 filed Nov. 29, 2001 and U.S. application Ser. No. 60/337,914 filed Dec. 6, 2001; the contents of both are hereby incorporated by reference in their entirety.

The invention relates to a portable delivery device, cartridge therefore and system suitable for subcutaneous or intra-dermal delivery of a flowable formulation of an active ingredient such as insulin.

BACKGROUND OF THE INVENTION

Medicament delivery devices for delivering medicaments to a patient generally comprise a reservoir for the medicament and driving means for delivering the medicament to the patient. The reservoir can be pre-filled with a medicament, or the device can be provided with means for filling the reservoir. The reservoir may be configured in many different ways; however, general types of reservoirs can be identified.

The best known and mostly used type of injection device for the treatment of different medical conditions, such as insulin treatment of type 1 or 2 diabetes, is the "pen"-formed device where the pen can be considered a manually actuated pump serving as the delivery means for a drug contained in a cartridge, generally in the form of a non-deformable cylindrical or columnar syringe comprising a displaceable piston. Although originally designed for the pen-type of devices, this type of reservoir has also been used in delivery pump devices comprising driving means allowing the drug to be expelled from the reservoir in a controlled manner. Although conventional drug cartridges are relatively inexpensive, their use in drug delivery devices has hitherto been associated with a number of disadvantages such as difficulties in modifying the general cylindrical form or the problems associated with the mechanical plunger means for driving the piston, such plunger driving means being both expensive and bulky adding to the cost and size of the delivery device. Other means than driving the piston by a mechanically advanced plunger have been suggested and will be discussed below.

Another type of reservoir is in the form of an expansible-contractible chamber arranged within a housing member, the interior of the housing including a flexible liquid-impermeable membrane defining a first expansible-contractible chamber between it and a first non-deformable section of the housing, and a second expansible-contractible chamber defined between it and a second non-deformable section of the housing. The first chamber serves as a reservoir for receiving the drug to be delivered, whereas the second chamber typically serves as a gas-pumping chamber for controlling the delivery of the drug from the reservoir. An example of such a reservoir is disclosed in U.S. Pat. No. 5,527,288.

A further type of reservoir is in the form of a flexible bag, however, although many i.v. infusion drugs are supplied in such containers, they have hitherto not been used extensively as reservoirs in portable delivery pump devices.

With respect to the driving means for moving a drug out of a container, in principle two different driving approaches can be used, i.e. either "pushing" or downstream "sucking".

"Pushing" in this respect covers any action which by reducing the internal volume of a reservoir drives out the therein contained drug. The pushing means may be in the form of mechanical means, for example a motor driven plunger rod acting on a piston in a cylinder reservoir as described above, or it may be in the form of gas generating means, in which case the gas may act on an expansible-contractible chamber as described above with respect to U.S. Pat. No. 5,527,288, or the gas may act directly on a piston in a cylinder reservoir as disclosed in WO 98/57683.

A further dispensing device based on gas generating means is known from U.S. Pat. No. 5,938,640 disclosing a dispenser comprising a variable-volume drug reservoir and a small water reservoir, the water being conducted to a gas-generating pump where it is used for producing a metered amount of a gas which subsequently is used to expel drug from the drug reservoir. The drug and water reservoirs are provided in a reservoir module and the gas-generating pump is provided in a pump module.

As appears, the gas generating means and the associated connecting means for allowing the gas to act on the reservoir provides for a relatively flexible design in which the actual form and configuration of the different components may be adapted specifically to fit the actual specification for a given delivery device. However, a major disadvantage associated with gas-based driving means is the susceptibility to pressure changes in the surrounding environment of use. More specifically, a pressure drop outside the gas-pumping chamber will result in expansion of the therein contained gas which inevitably will result in uncontrolled expelling of drug from the reservoir. Evidently, such a situation is not merely hypothetical but will take place during, for example, a flight in an aeroplane without pressure cabin or during mountain walking or climbing. Also normal atmospheric depressions may of an order which will influence the function of the device. Contrary, a pressure rise will result in a corresponding compression of the gas in the gas-driving chamber and consequently result in a diminished amount of drug being supplied to the patient. Evidently, it would be possible to prevent such undesired consequences of external pressure variations, for example by stopping gas generation and sealing off the gas pumping chamber, however, to provide the necessary valve means, pressure sensor means and control means would considerably add to the complexity and cost of the delivery device, just as a closed-down system would be non-functional until "normal" pressure conditions are re-established. Indeed, it would be possible to operate such a system also under varying external pressure condition, however, this would necessitate controlling the actual output flow, this further adding to the complexity.

A different principle is known from DE-A1-37 39 657 disclosing a bedside infusion set-up. In order to avoid the need for a traditional pump a syringe plunger rod is hydraulically driven. More specifically, a flexible bag containing a drive liquid is suspended over the syringe and fed by gravitational force to a chamber moving the plunger, this providing a simple pump means.

"Sucking" in this respect covers any action by which a drug is drawn from a reservoir by applying a negative pressure (relative to the pressure in the reservoir) to an outlet opening of the reservoir. A traditional type of pump used in the context of administering a drug or fluid to a patient is the peristaltic pump acting on a flexible tube portion, this arrangement preventing the pump means (except for the tube) to come into contact with the drug. FR-A-2 753 103 discloses a medical pump device incorporating such a peristaltic pump.

Another type of pump used in this context is the conventional valve pump comprising a displacing structure (e.g. a piston or a pump membrane) cooperating with inlet and outlet valves. Such a pump may be formed with separate actuation means driving the valves and the displacing structure formed integrally with a disposable reservoir and its associated tubing, or it may be in the form of a micro pump in direct contact with the drug. The latter type of pump would mainly be relevant as a disposable unit as the need for cleaning a pump is not considered desirable Depending on the type of suction pump used, a number of disadvantages are associated therewith. Depending on the type of reservoir used, it may be necessary to apply very high (relative) negative pressures, for example when drawing a drug from a conventional syringe-piston cartridge. In fact, many such standard cartridges have a frictional resistance between the (rubber) piston and the (glass) cylinder wall which could not be overcome even by an absolute vacuum provided by the pump. Pumps relying on a disposable portion in contact with the drug and a durable pump drive means are typically bulky as well as expensive, whereas an integrated disposable micro pump would add to the cost of the disposable cartridge as such.

A further problem when using a suction pump is the risk for damaging a pressure sensitive drug as it is sucked through the pump, which especially is a problem when using micro pumps in which the drug is forced through narrow passageways. Another problem is the risk of contaminating the drug with substances from structures with which the drug comes into contact, e.g. the displacing structure and the valves. The other way round, the drug may also be harmful to these structures.

Having regard to the above discussion of known devices and systems, there exists a need for a new and improved concept for a delivery device and system which provide a high degree of safety, ease of use and compactness as well as a high degree of flexibility in respect of using different types of reservoirs without having to substantially redesign the delivery device and its different components. The device should be safe and reliable in use under most external pressure conditions, it should be gentle to the drugs to be infused as well as easy to use, compact in size and inexpensive to manufacture. Further, the general concept should allow the manufacturer to provide a high degree of flexibility in a cost effective and efficient manner.

Correspondingly, it is an object of the present invention to provide a pump which overcomes one or more of the identified deficiencies and provides a solution to one or more of the identified needs.

SUMMARY OF THE INVENTION

The present invention is based on the principle that a first reservoir for a flowable drug is provided in combination with a second reservoir comprising a pump liquid, a pump chamber being associated with the first reservoir and adapted to receive the pump liquid in order to expel drug from the first reservoir.

More specifically, in a first aspect of the invention a cartridge for a delivery device comprises a variable-volume drug reservoir comprising outlet means and adapted for containing a pre-defined volume of a flowable drug, a pump liquid reservoir comprising a volume of a pump liquid contained therein and a pump liquid outlet means, and a variable-volume pump chamber associated with the drug reservoir and comprising a pump liquid inlet means, the pump chamber being adapted to receive the pump liquid in order to expel a drug from the drug reservoir as the pump chamber expands. In order to substantially expel all drug contained in the drug reservoir, the volume of the pump liquid corresponds at least to the volume for which the drug reservoir is adapted. When in certain circumstances it would be desirable to leave a given (small) amount of drug in the reservoir or when it for constructional reasons is not possible to fully empty the drug reservoir, the definition that the volume of the pump liquid corresponds at least to the volume for which the drug reservoir is adapted should be construed as including situations in which the volume of the pump liquid is somewhat less than the volume for which the drug reservoir is adapted (e.g. 30% smaller). The pump liquid may be any suitable liquid which is not harmful to the materials with which it comes into contact.

The drug reservoir may be pre-filled with the liquid to be infused and thus ready to be used, or it may be adapted to be filled with the liquid from an external source prior to use, the latter in case a pre-filled reservoir will result in reduced shelf-life for the contained liquid.

In a second aspect of the invention, the above "basic" components are provided as a cartridge unit to be combined with one or more further units to form a system, the system as a whole comprising the pump means for pumping the pump liquid from the second reservoir to the pump chamber, control means for controlling the action of the pump means, and an energy reservoir for energizing the pump means as well as the control means, however, one or more of these components may be incorporated in the cartridge. The cartridge may be intended for single use (being either pre-filled or fillable) or adapted to be filled a number of times. In the latter case the pump liquid reservoir may be pre-filled comprising a volume of a pump liquid sufficient for emptying a number of reservoirs, however, the pump liquid reservoir may also be fillable or refillable. The cartridge may be supplied with an energy source, pump means, control means or any combination thereof, either for single or multiple use. In case all of these components are provided in a disposable unit, the further unit(s) of the system may serve mainly as a platform comprising, for example, a user interface having a display and/or programming means allowing the user to enter user specific settings, or means for wireless communication with a remote unit comprising display and/or control means. The units may be adapted for wireless communication either uni- or bi-directionally. The pump may be operated continuously to provide a basal infusion rate (having a constant or variable profile), part-continuously in accordance with a given infusion scheme, non-continuously to provide bolus delivery in accordance with user actuation or other instructions, or continuously providing both basal rate and bolus delivery.

In a third aspect, the system may be provided as a single self-contained disposable delivery device, the flexibility inherent in the system allowing a manufacturer to modify the system in a cost-effective manner. Although self-contained, such a disposable unit may be provided with communication means (e.g. wireless communication means) allowing the unit to communicate with an optional remote unit, the two units being adapted for (wireless) communication either uni- or bi-directionally.

The pump may be of any suitable type but in exemplary embodiments the pump is of the "metering" type, allowing the amount of drug infused to be controlled solely by controlling the action of the pump as discussed above (e.g. controlling actuation of a displacing structure such as a piston or a pump membrane, or controlling gas generation) without the need for downstream flow sensors and corresponding feedback control, however, non-metering pumps in combination with flow sensors and corresponding control means may also be used. Examples of suitable membrane pumps are disclosed and discussed in U.S. Pat. No. 6,280,148 and in a paper by D. Maillefer et al, "A high-performance silicon micropump for disposable drug delivery systems", Debiotec SA, Switzerland, both incorporated by reference. These micropumps are based on pump membranes manufactured from silicon, however, pump membranes may also be manufactured from polymers (e.g. plastic and rubber materials).

The drug-containing reservoir may be provided as any of the initially discussed types; however, the pump chamber will have to be adapted correspondingly. For example, for a reservoir of the columnar type comprising a piston, the pump chamber could be established between the piston and a closed rear portion of the syringe. In case the reservoir is of the expansible-contractible chamber type arranged within a housing member, the above-described second chamber may serve as a pump chamber for receiving the pump liquid (instead of a gas). When the reservoir is in the form of a flexible bag, the bag should be enclosed entirely within a housing, the space established between the outer surfaces of the bag and the housing defining the pump chamber. Indeed, in all cases the pump chamber is provided with inlet means for the pump liquid just as the reservoir is provided with outlet means for the drug to be expelled.

The terms inlet and outlet means merely indicate that a suitable structure is provided allowing the desired flow of liquid in a situation of use. These means may be provided by any type of openings or conduits having openings, just as the openings may be provided with valve means or closed or sealed in any suitable way allowing the desired liquid communication with external means such as pumps and associated delivery means, e.g. catheters or hollow needles, to be established in a situation of use. The term non-deformable is used to indicate that any inevitable but minimal deformation from a practical and functional aspect can be neglected.

The second reservoir comprising the pump liquid may in principle also be provided as any of the above-discussed reservoir types, however, to avoid frictional problems and to avoid the need for venting the reservoir, the second reservoir is preferably of the contractible or collapsible type allowing the pump liquid to be pumped (sucked) out substantially without any pumping resistance.

The reservoir outlet means may be adapted to be brought in fluid communication with infusion means (e.g. a catheter tubing or transcutaneous access means such as an infusion needle, a flexible infusion cannula or a plurality of micropenetrators) or may comprise these. In the latter case the fluid communication may be established just prior to use, before or after the drug delivery device has been arranged relative to a user.

In case the cartridge is supplied as a disposable unit (or a self-contained disposable delivery device is provided), it may comprise a mounting surface adapted for application to the skin of a subject, the mounting surface advantageously comprising a pressure-sensitive adhesive which allows the cartridge or device to be affixed to the skin of the subject user. In case a cartridge is provided with adhesive means, the cartridge preferably provides a mounting basis for a cooperating control unit such that only the cartridge is in contact with the skin of the user. The outlet means of the cartridge or delivery device may comprise a hollow infusion needle communicating, in a situation of use, with the interior of the drug reservoir, the infusion needle comprising a distal pointed end adapted to penetrate the skin of the subject. The infusion needle may be moveable between a first position in which the pointed end of the needle is arranged in a retracted position relative to the mounting surface, and a second position in which the pointed end of the needle projects from the mounting surface. Examples of suitable arrangements for needle insertion are disclosed in, for example, U.S. Pat. Nos. 4,886,499 and 6,074,369 incorporated by reference.

In a further aspect of the present invention, a method for infusing a flowable drug into a living subject is provided, comprising the steps of providing a cartridge or delivery device having a variable-volume drug reservoir containing a flowable drug and comprising an outlet means, a pump liquid reservoir comprising a pump liquid contained therein and a pump liquid outlet means, and a variable-volume pump chamber associated with the drug reservoir and comprising a pump liquid inlet means, the pump chamber being adapted to receive the pump liquid in order to expel the drug from the drug reservoir as the pump chamber expands, the method comprising the further steps of establishing a flow connection between the outlet means and the subject, and pumping pump liquid from the pump liquid reservoir into the pump chamber to thereby expel the drug from the drug reservoir and into the subject. In exemplary embodiments, the cartridge and/or delivery device as described herein is used.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals (including peptides, proteins, and hormones), biologically derived or active agents, hormonal and gene based agents, nutritional formulas and other substances in both solid (dispensed) and liquid form. In the description of the exemplary embodiments reference will be made to the treatment of diabetes by infusion of insulin, however, this is only an exemplary use of the present invention. Correspondingly, the term "subcutaneous or intra-dermal delivery" is meant to encompass any method of parenteral delivery to a subject.

BRIEF DESCRIPTION OF THE DRAWINGS

In the following the invention will be further described with references to the drawings, wherein FIGS. 7A and 7B show a cartridge and mating pump unit, wherein the pump chamber and the associated pump liquid inlet and outlet means in an initial state have a volume of substantially zero.

DESCRIPTION OF EXEMPLARY EMBODIMENTS

Figure 1:
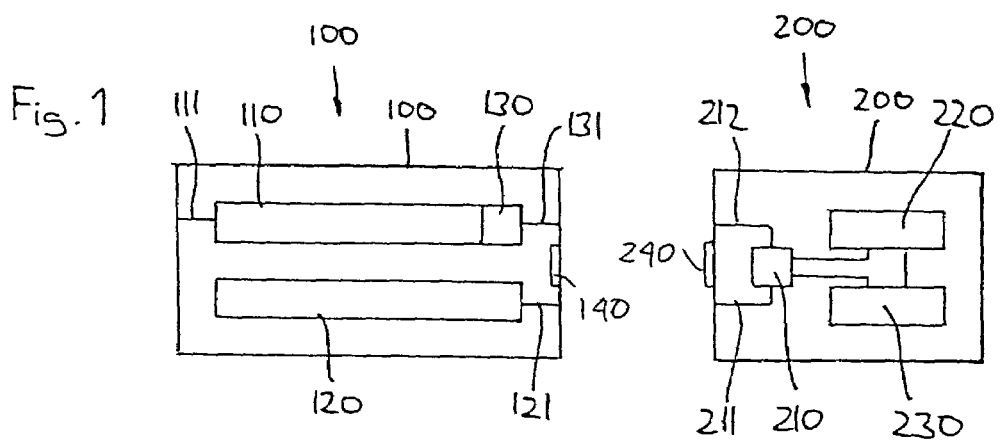
FIG. 1 shows a schematic representation of a first embodiment of a cartridge unit in accordance with the invention, and a corresponding pump unit.

FIG. 1 shows a schematic representation of an embodiment of disposable cartridge unit 100 in accordance with the invention and a corresponding pump unit 200 adapted to be used in combination with the cartridge. The cartridge comprises a housing 101 with a first drug reservoir 110 having a drug outlet 111, a second pump liquid reservoir 120 having a pump liquid outlet 121, and a pump chamber 130 associated with the first reservoir and having a pump liquid inlet 131. The pump chamber may initially be "virtual", i.e. fully collapsed as discussed below.

The drug reservoir defining an interior for accommodating a drug is of the variable volume type comprising a flexible or moveable portion such that an inwardly directed movement thereof will result in a reduced volume and thereby expelling of the contained drug. Correspondingly, the pump chamber defining an interior for accommodating the pump liquid is also of the variable volume type comprising a flexible or moveable portion in communication with the flexible or moveable portion of the drug reservoir such that an outwardly directed movement thereof will result reduce the volume of the drug container. The flexible or moveable portion may be represented by a common element having opposed surfaces facing the interior of the drug reservoir and the pump chamber respectively.

The pump liquid reservoir is preferably of the contractible or collapsible type allowing the pump liquid to be pumped (or sucked) out substantially without any pumping resistance without the need for venting the reservoir.

The different in- and outlets each comprises an external opening adapted to communicate with corresponding liquid conducting means when connected thereto. The openings preferably comprises closure means sealing the openings in their non-connected state, the closure means allowing liquid communication to be established between the in- and outlets and the corresponding liquid conducting means when connected thereto.

The pump unit 200 comprises a housing 201 with a pump 210 having an inlet 211 and an outlet 212 with respective external openings, control means 220 connected to the pump for control thereof, and an energy source 230 for supplying energy to the pump and control means. The pump unit may further be provided with user-accessible programming means, display means, memory means as well as communication means allowing the pump unit to communicate with external units either by wire or wirelessly (not shown).

Figure 2:
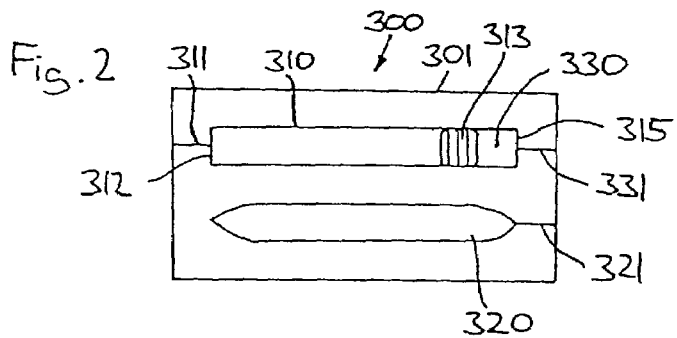
FIG. 2 shows a second embodiment of a cartridge unit.
Figure 3:
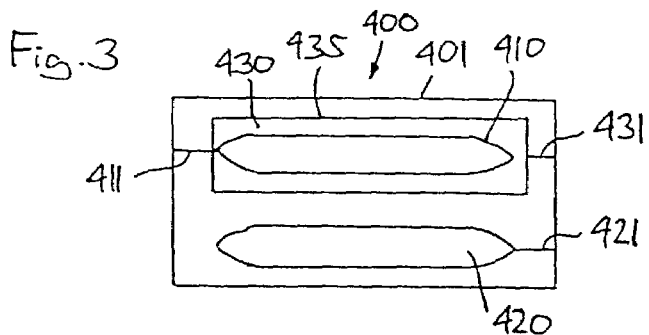
FIG. 3 shows a third embodiment of a cartridge unit.
Figure 4:
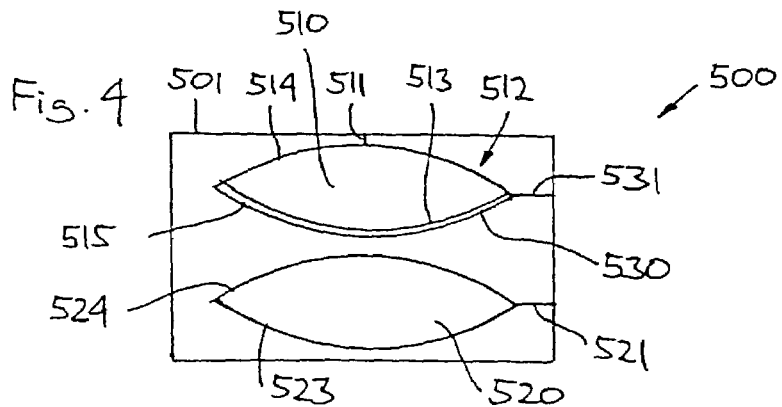
FIG. 4 shows a fourth embodiment of a cartridge unit.

The cartridge unit and the pump unit further include schematically shown mating coupling means (140, 240) so as to allow the units to be secured to each other (the corresponding coupling means for the cartridges of FIGS. 2-4 are not shown), thereby establishing liquid communication between the pump liquid outlet 121 and the pump inlet 211, as well as between the pump outlet 212 and the pump liquid inlet 131.

FIG. 2 shows a second embodiment of a cartridge unit 300 in accordance with the invention. The cartridge comprises a housing 301 with a drug reservoir 310 having an outlet 311, a pump liquid reservoir 320 having a pump liquid outlet 321, and a pump chamber 330 having a pump liquid inlet 331.

The drug reservoir is basically in the form of a cylindrical syringe-like member comprising a circumferential wall and a front-end portion 312 in communication with the outlet, an axially displaceable piston 313 being arranged within the cylinder in sliding and sealing engagement with the interior surface of the wall, thereby defining a variable-volume interior for accommodating a drug. The cylindrical member further comprises a rear end portion 315 in communication with the outlet 331, the pump chamber thereby being established between the rear end portion and the piston, expansion of the pump chamber resulting in forwards movement of the piston. It is to be noted that the pump chamber in the illustrated state is fully filled with pump liquid as any enclosed gas would jeopardize the metered expelling of drug. The drug reservoir may be in the form of a modified standard glass cartridge for a traditional pen-formed injection device, the front end portion being formed integrally with the wall and having an outlet and corresponding closure means in the form of a needle-penetratable flexible membrane, and the piston being of the type normally driven by a plunger. The modification substantially relies in a rear closure member being arranged corresponding to the rear opening of the cylinder, for example by sealingly bonding the closure member within the opening. Preferably the inlet 331 and the corresponding closure means are provided integrally formed with the closure member, e.g. by a penetratable flexible membrane. An advantage of the traditional glass cartridge is the long shelf life which can be obtained for drugs stored therein, this due to the fact that many drugs are "inert" to a glass surface, whereas most polymeric surfaces will react with the drug, thereby reducing shelf life.

The pump liquid reservoir 320 is in the form of a flexible bag comprising opposed flexible sheets sealingly attached to each other at the peripheries thereof thereby defining an interior for the pump liquid, the flexibility of the bag allowing the pump liquid to be pumped out substantially without any pumping resistance through an outlet 321 which may be closed by the same type of means as described above.

As appears from above, the in- and outlets as well as their corresponding closure means are preferably formed integrally with the reservoirs and the chamber, this making it clear that the shown "conduits" 311, 321, 331 are merely provided for illustrative purposes which, indeed, also apply to the packaging of the cartridge unit; especially the flexible pump liquid reservoir would allow the cartridge to be densely packed and configured to meet a desired form configuration.

FIG. 3 shows a third embodiment of a cartridge unit 400 in accordance with the invention. The cartridge comprises a housing 401 with a drug reservoir 410 having an outlet 411, a pump liquid reservoir 420 having a pump liquid outlet 421, and a pump chamber 430 having a pump liquid inlet 331.

The drug reservoir 410 is in the form of a flexible bag comprising opposed flexible sheets sealingly attached to each other at the peripheries thereof thereby defining an interior for the drug. The drug reservoir is fully enclosed within a non-deformable chamber housing 435, a pump chamber 430 thereby being defined between the exterior surface of the drug reservoir and the interior wall of the surrounding housing. In case the drug reservoir initially does not fully occupy the chamber housing thereby reducing the pump chamber volume to substantially zero, then an "initial" chamber (as shown) should be supplied pre-filled with pump liquid.

The pump liquid reservoir 420 is in the form of a flexible bag as described with respect to FIG. 2. Correspondingly, the in- and outlets as well as their corresponding closure means are preferably formed integrally with the reservoirs and the chamber.

FIG. 4 shows a fourth embodiment of a cartridge unit 500 in accordance with the invention. The cartridge comprises a housing 501 with a drug reservoir 510 having an outlet 511, a pump liquid reservoir 520 having a pump liquid outlet 521, and a pump chamber 530 having a pump liquid inlet 531.

The drug reservoir is formed integrally with the pump chamber as combined expansible-contractible chambers arranged within a common housing member 512, the interior of the housing including a first flexible liquid-impermeable membrane 513 defining a first expansible-contractible chamber (serving as the drug reservoir) between it and a first non-deformable section 514 of the housing, and a second expansible-contractible chamber (serving as the pump chamber) defined between it and a second non-deformable section 515 of the housing. Preferably the two chambers and the flexible membrane are formed such that membrane can be shifted between an initial position in which the pump chamber is entirely empty and a final position in which the drug reservoir is entirely empty.

The pump liquid reservoir 520 is correspondingly formed between a non-deformable housing section 524 and a second flexible liquid-impermeable membrane 523. In order to allow the membrane to freely collapse as the pump liquid is sucked out by the pump means, the rear surface of the membrane is vented to the exterior (not shown).

With reference to FIGS. 2-4 embodiments comprising different configurations for the drug reservoir respectively the pump liquid reservoir have been described, however, it is clear that the different reservoirs and chambers could be combined as desired.

As mentioned above, it is important for a properly controlled pump function that substantially no gas (air) is pumped into or trapped in the pump chamber. In order to avoid this, the pump and the associated pump in- and outlets have to be primed with pump liquid. This may be done during manufacture such that the pump unit is supplied to the end-user primed with a pump liquid, which may be the same or a different liquid as the one supplied in the cartridge unit. The pump unit may also be supplied with a special priming unit similar to a cartridge unit (i.e. comprising at least a small pump liquid reservoir) which would allow the pump to be primed during an initial priming operation after which a proper cartridge unit may be mounted.

Also the pump chamber as well as the associated in- and outlets have to be free from gas. This may be accomplished by more or less complicated priming/venting procedures (either performed during manufacture or by the end user) or, more effectively, avoided by providing a cartridge unit with "zero dead-space", i.e. the pump chamber and the associated pump liquid in- and outlets are supplied in a fully collapsed state, an exemplary embodiment of which will be described with reference to FIGS. 7A and 7B.

More specifically, FIG. 7 shows a cartridge 1 (shown in partial) comprising a drug reservoir 10 having a drug outlet (not shown), a moveable piston 11 and a first end plug 12 with a through-going collapsed bore 13, the piston and the plug having corresponding surface portions facing each other such that a collapsed pump chamber 15 is established between the piston and the plug when positioned against each other as shown in the figure, the bore serving as a pump liquid inlet 16 for the pump chamber. In case the drug reservoir is adapted to be filled from an external source prior to use, this situation would correspond to the filled drug reservoir. The cartridge further comprises a pump liquid reservoir 20 having a second end plug 22 with a through going collapsed bore 23, the bore serving as a pump liquid outlet 26 from the pump liquid reservoir. The pump unit 2 (shown in partial) comprises a pump (not shown) having inlet and outlet means comprising connecting tube members 30, 40 projecting from the pump unit and adapted to engage the corresponding pump liquid outlet and inlet. More specifically, each tube member is adapted to be fully inserted into the corresponding collapsed bore thereby establishing liquid communication between the pump liquid outlet and the pump inlet, respectively the pump liquid inlet and the pump outlet. As the pump as well as the tube members have been primed prior to insertion (whereby capillary action prevents liquid from escaping the tube members), a fully primed liquid connection has been established between the two reservoirs 10, 20 as seen in FIG. 7B further illustrating the pump chamber being partially filled with pumped-in liquid.

In the above described embodiment blunt tube members are inserted in collapsed bores, however, other suitable arrangements could be envisaged, e.g. a hollow needle could be inserted through a self-sealing penetratable membrane.

Figure 5:
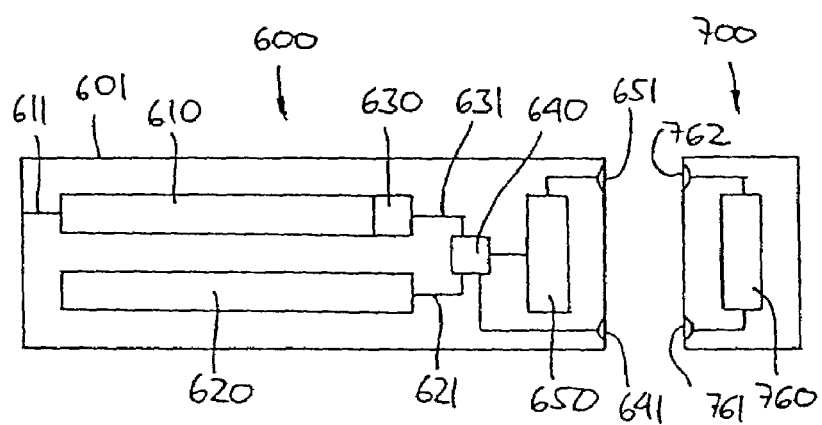
FIG. 5 shows a further embodiment of a cartridge unit corresponding to the invention in combination with a mating control unit.

FIG. 5 shows a further embodiment of a cartridge unit 600 corresponding to the invention in combination with a corresponding control unit 700. The cartridge comprises a housing 601 with a drug reservoir 610 having an outlet 611, a pump liquid reservoir 620 having a pump liquid outlet 621, and a pump chamber 630 having a pump liquid inlet 631, which components may be configured substantially as described above with reference to FIGS. 1-4. However, in contrast to these embodiments, the cartridge unit 600 further comprises a pump 640 having a pump inlet in communication with the pump liquid outlet and an outlet in communication with the pump liquid inlet, and an energy source 650 for supplying energy to the pump and control means (to be described).

In an exemplary embodiment the pump is a membrane pump. Such a pump can be made very compact and can provide linear and accurate pumping with a stroke volume of, for example, as little as 160 nl. These pumps are suitable for disposable use, but may also be adapted for more durable use in a non-disposable control unit.

The control unit 700 comprises control means 760 for controlling the operation of the pump, the two units further comprising mating coupling means so as to allow the control unit to be secured to the cartridge unit, the mating coupling means including communication means 641, 761 allowing the control means to communicate with the pump as well as electric contacts 651, 762 for transferring energy to the control unit. The control unit may further be provided with user-accessible programming means, display means as well as memory means (not shown). It would be possible to divide the control means in "higher" and "lower" level control means, whereby the lower level control means could be integrated with the pump, the higher level control means allowing, for example, programmability and communication with the user.

As the drug and the corresponding pump liquid is provided as a single, integral "dual-volume" unit, it would be possible to replace a first cartridge with a second type of cartridge (e.g. containing a different kind of drug) for later re-installing the first cartridge. In this context the cartridge unit may further comprise a memory keeping an account of the amount of liquid left in the reservoir. By enclosing such a memory in the cartridge unit containing the liquid reservoir, this memory is firmly connected to the reservoir. This is appropriate if the memory shall be able to keep an account of the amount of liquid left in the reservoir. Data in the memory may be read out by the control unit and represented on a display. Such a memory may be provided in a cartridge with or without a pump and or an energy source included, however, a battery backup would be necessary.

As the actual drug delivery is based purely on the pumped volume, it may be desirable to "translate" the infused drug volume into, for example, units of insulin, upon which control of the pump may be based. However, this would necessitate that information regarding the drug contained in the actual cartridge is communicated to the control means. Therefore, the cartridge preferably comprises indicia which can be "read" by the control unit, such indicia being either electronically represented data contained in memory means, or represented by mechanical means which can be detected by the control unit. The mechanical indicia means may cooperate with any suitable kind of contact means in the control unit, e.g. electrical contacts or opto-electrical means.

Figure 6:
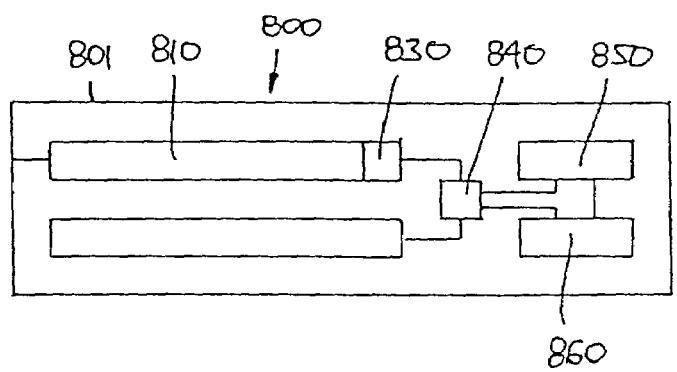
FIG. 6 shows an integrated self-contained delivery device.

FIG. 6 shows a further embodiment of the invention in which the different components of the system described in FIG. 5 has been integrated into a self-contained delivery device 800. More specifically, the injection device comprises a housing 801 with a drug reservoir 810, a pump liquid reservoir 820, a pump chamber 830, a pump 840 having a pump inlet in communication with a pump liquid outlet and an outlet in communication with a pump liquid inlet, an energy source 850 for supplying energy to the pump and control means, and control means 860 for controlling the operation of the pump. Although such a self-contained disposable unit to the end-user may appear to be provide no flexibility, the flexibility inherent in the system would allow a manufacturer to modify the system in a cost-effective manner, e.g. a wide variety of drugs, drug containers, container sizes etc. may be used without the need for redesigning the system, this capability being based on the "dual-reservoir" principle allowing a single pump layout to be used in combination with different cartridges (either replaceable or integrated).

In the different embodiments described above, the drug reservoir outlet means may comprise an outlet port comprising coupling means so as to allow an infusion catheter or a hollow infusion needle to be attached thereto, or the cartridge may be supplied with a needle or catheter formed integrally therewith. Such a connector may also serve as a port for filling the reservoir, either initially or during re-filling, however, refilling would considerably complicate construction of the cartridge due to complicated venting/priming operations.

While the present invention has been described in connection with the exemplary embodiments shown in the various figures, the delivery device according to the invention may be provided with additional features providing improved functionality, control and ease of use.

For example, a sensor may be provided for continuously measuring the pressure in the pump outlet, this allowing the detection of a malfunctioning which could be used to initiate an alarm making the user aware of a problem.

However, more advanced sensors may be incorporated in the device. For example, it may be desirable to automatically deliver certain drugs only when required by the subject, either by patient activation or passively, such as by a closed loop feedback mechanism. In such a case, the device further includes a sensor for detecting a condition in the body of the subject and for controlling the delivery of the drug in response thereto. The sensor may be, for example, a temperature sensor, a pulse rate sensor, a blood glucose sensor, a blood pressure sensor or a pH sensor. The sensors may be formed integrally with the disposable unit or attached separately. The sensor may rest against the skin, may be inserted through the skin, or may be within the device and separate from the skin.

The disposable unit may also include a plurality of drug reservoirs and corresponding pump liquid reservoirs, each reservoir being independently controllable and communicating with an outlet cavity with which a single infusion needle also communicates. For such a plurality of drug reservoirs, pump means integrally formed with the cartridge unit may be used. Including a plurality of drug reservoirs provides for considerable variations in the amounts of drug which can be delivered, in the rates at which drug can be delivered and in the number of drugs which can be delivered by the same device. The cartridge unit may further be provided with a reservoir for a calibrating liquid in case the unit is provided with sensors requiring such a liquid.

The control unit may be provided with means allowing remote communication. For example, the control unit may transmit signals indicative of the amount and profile of drug infused or left in the reservoir, the signals being picked up by a remote unit carried by the user allowing the user easy access to the data. The data may also be distributed to persons responsible for treatment of the user.

In the above description of the exemplary embodiments, the different structures providing mechanical, electrical and fluid contact and communication between the different components just as the means providing the described functionality for the different components (i.e. pump, reservoir, energy source, memory, control, display etc.) have been described to a degree to which the concept of the present invention will be apparent to the skilled reader. The detailed construction and specification for the different components are considered the object of a normal design procedure performed by the skilled person along the lines set out in the present specification.

The invention claimed is:

1. A cartridge for a delivery device, the cartridge comprising:
   a variable-volume drug reservoir comprising an outlet and adapted for containing a predefined volume of a flowable drug,
   a pump liquid reservoir comprising a volume of a pump liquid contained therein and a pump liquid outlet allowing liquid to be expelled out of the cartridge, the pump liquid outlet being adapted to be connected to an inlet of a pump arranged outside the cartridge,
   a variable-volume pump chamber associated with the drug reservoir and comprising a pump liquid inlet allowing the variable-volume pump chamber to receive liquid from outside the cartridge, the pump liquid inlet being adapted to be connected to an outlet of a pump arranged outside the cartridge, the pump chamber being adapted to receive the pump liquid in order to expel a drug from the drug reservoir as the pump chamber expands,
   wherein the volume of the pump liquid corresponds at least to the volume for which the drug reservoir is adapted.

2. A cartridge as in claim 1, wherein the drug reservoir is in the form of a substantially cylindrical body with an axially displaceable piston arranged there within, the piston and the pump chamber being arranged such that expansion of the pump chamber displaces the piston axially.

3. A cartridge as in claim 1, wherein the drug reservoir is in the form of a flexible bag, the drug reservoir being enclosed within a non-deformable chamber housing, the pump chamber being defined between an exterior surface of the drug reservoir and an interior wall of the surrounding chamber housing.

4. A cartridge as in claim 1, comprising a housing member having first and second non-deformable sections and a flexible liquid-impermeable membrane defining the drug reservoir between the membrane and the first non-deformable section, and defining the pump chamber between the membrane and the second non-deformable section, whereby expansion of the pump chamber will result in reduction of the volume of the drug reservoir.

5. A cartridge as in claim 1, wherein the pump liquid reservoir is in the form of a flexible bag, or is formed between a non-deformable housing section and a second flexible liquid-impermeable membrane.

6. A cartridge as in claim 1, wherein at least one of the inlet and outlet comprises an opening closed by a penetratable self-sealing membrane.

7. A cartridge as in claim 1, wherein the drug reservoir contains a volume of a flowable drug, the volume of the pump liquid corresponding at least to the volume of the flowable drug.

8. A cartridge for a delivery device, the cartridge comprising:
   a variable-volume drug reservoir comprising an outlet and adapted for containing a predefined volume of a flowable drug,
   a liquid-impermeable pump liquid reservoir comprising a volume of a pump liquid contained therein and a pump liquid outlet allowing liquid to be expelled out of the cartridge, the pump liquid outlet being adapted to be connected to an inlet of a pump arranged outside the cartridge, a variable-volume pump chamber associated with the drug reservoir and comprising a pump liquid inlet allowing the variable-volume pump chamber to receive liquid from outside the cartridge, the pump liquid inlet being adapted to be connected to an outlet of a pump arranged outside the cartridge, the pump chamber being adapted to receive the pump liquid in order to expel a drug from the drug reservoir as the pump chamber expands, wherein the volume of the pump liquid corresponds at least to the volume for which the drug reservoir is adapted.

9. A cartridge as in claim 8, wherein the drug reservoir is in the form of a substantially cylindrical body with an axially displaceable piston arranged there within, the piston and the pump chamber being arranged such that expansion of the pump chamber displaces the piston axially.

10. A cartridge as in claim 8, wherein the drug reservoir is in the form of a flexible bag, the drug reservoir being enclosed within a non-deformable chamber housing, the pump chamber being defined between an exterior surface of the drug reservoir and an interior wall of the surrounding chamber housing.

11. A cartridge as in claim 8, wherein the pump liquid reservoir is in the form of a flexible bag.

12. A cartridge for a delivery device, the cartridge comprising:

a variable-volume drug reservoir comprising an outlet and adapted for containing a predefined volume of a flowable drug, a contractible or collapsible pump liquid reservoir comprising a volume of a pump liquid contained therein and a pump liquid outlet allowing liquid to be expelled out of the cartridge, the pump liquid outlet being adapted to be connected to an inlet of a pump arranged outside the cartridge, a variable-volume pump chamber associated with the drug reservoir and comprising a pump liquid inlet allowing the variable-volume pump chamber to receive liquid from outside the cartridge, the pump liquid inlet being adapted to be connected to an outlet of a pump arranged outside the cartridge, the pump chamber being adapted to receive the pump liquid in order to expel a drug from the drug reservoir as the pump chamber expands, wherein the volume of the pump liquid corresponds at least to the volume for which the drug reservoir is adapted.

13. A cartridge as in claim 12, wherein the drug reservoir is in the form of a substantially cylindrical body with an axially displaceable piston arranged there within, the piston and the pump chamber being arranged such that expansion of the pump chamber displaces the piston axially.

14. A cartridge as in claim 12, wherein the drug reservoir is in the form of a flexible bag, the drug reservoir being enclosed within a non-deformable chamber housing, the pump chamber being defined between an exterior surface of the drug reservoir and an interior wall of the surrounding chamber housing.

15. A combined portable delivery device comprising a cartridge and a control unit, wherein the cartridge and the control unit include mating coupling means so as to allow the cartridge to be secured to the control unit, the combined delivery device comprising:

a variable-volume drug reservoir comprising an outlet and adapted for containing a flowable drug, a pump liquid reservoir comprising a pump liquid contained therein and a pump liquid outlet, a variable-volume pump chamber associated with the drug reservoir and comprising a pump liquid inlet, the pump chamber being adapted to receive the pump liquid in order to expel a drug from the drug reservoir as the pump chamber expands, the drug reservoir, the pump liquid reservoir and the pump chamber being comprised in the cartridge, a pump arranged for receiving pump liquid from the pump liquid outlet and for pumping the pump liquid from the pump liquid reservoir to the pump chamber via the pump liquid inlet, control means comprised in the control unit for controlling the operation of the pump, an energy source for operating the pump and/or the control means, and the mating coupling means providing communication between the pump and the pump liquid outlet and inlet, or between the control means and the pump.

16. A delivery device as in claim 15, wherein the volume of the pump liquid corresponds at least to the volume for which the drug reservoir is adapted.

* * * * *